(12) United States Patent
Matthis et al.

(10) Patent No.: US 9,144,437 B2
(45) Date of Patent: Sep. 29, 2015

(54) BONE ANCHORING ASSEMBLY (75) Inventors: Wilfried Matthis, Weisweil (DE); Lutz Biedermann, VS-Villingen (DE); Gerhard Pohl, St. Georgen (DE)

(73) Assignee: Biedermann Technologies GmbH & Co. KG, Donaueschingen (DE)

(*) Notice: Subject to any disclaimer, the term of this patent is extended or adjusted under 35 U.S.C. 154(b) by 664 days.

(21) Appl. No.: 12/488,458

(22) Filed: Jun. 19, 2009

(65) Prior Publication Data

US 2009/0318969 A1    Dec. 24, 2009

Related U.S. Application Data

(60) Provisional application No. 61/073,879, filed on Jun. 19, 2008.

(30) Foreign Application Priority Data

Jun. 19, 2008  (EP) .................................. 08 011 203

(51) Int. Cl.
*A61B 17/70* (2006.01)
(52) U.S. Cl.
CPC ......... *A61B 17/7031* (2013.01); *A61B 17/7032* (2013.01); *A61B 17/7037* (2013.01)
(58) Field of Classification Search
CPC .............. A61B 17/7037; A61B 17/704; A61B 17/7031; A61B 17/7032
USPC .................... 606/254, 255, 246–279
See application file for complete search history.

(56) References Cited

U.S. PATENT DOCUMENTS 5,261,912 A    11/1993  Frigg
5,360,431 A *  11/1994  Puno et al. ............... 606/308
(Continued)

FOREIGN PATENT DOCUMENTS

EP    1 759 646 A1    3/2007
EP    1 839 606 A1    3/2007
(Continued)

OTHER PUBLICATIONS

European Search Report for European Application No. 08011203.0. 1265. European Search Report dated Nov. 14, 2008 and mailed Nov. 24, 2008 (6 pgs.).

(Continued)

*Primary Examiner* — Eduardo C Robert
*Assistant Examiner* — Stuart S Bray
(74) *Attorney, Agent, or Firm* — Christie, Parker & Hale, LLP (57) ABSTRACT

A bone anchoring assembly includes a bone anchoring element having a shank to be anchored in a bone or a vertebra, and a receiving part for receiving a rod. The assembly includes a rod made at least partly of a material which exhibits a material flow under pressure. The receiving part includes a channel with an approximately U-shaped cross-section with two free legs, a first locking element cooperating with the legs to secure the rod in the channel, and a second locking element cooperating with the first locking element and acting independently from the first locking element onto the rod. A pin-shaped projection is provided at the second locking element which comes into contact with the rod when tightening the second locking element, and at least one pin-shaped projection is provided in the channel which comes into contact with the rod when tightening the first locking element.

18 Claims, 6 Drawing Sheets

(56) References Cited

U.S. PATENT DOCUMENTS

| | | | |
|---|---|---|---|
| 5,443,467 A | 8/1995 | Biedermann et al. | |
| 5,496,321 A | 3/1996 | Puno et al. | |
| 5,536,268 A | 7/1996 | Griss | |
| 6,102,913 A | 8/2000 | Jackson | |
| 6,179,841 B1 | 1/2001 | Jackson | |
| 6,224,596 B1 | 5/2001 | Jackson | |
| 6,224,598 B1* | 5/2001 | Jackson | 606/305 |
| 6,361,535 B2 | 3/2002 | Jackson | |
| 6,454,768 B1 | 9/2002 | Jackson | |
| 6,652,526 B1* | 11/2003 | Arafiles | 606/308 |
| 6,682,530 B2* | 1/2004 | Dixon et al. | 606/279 |
| 6,730,089 B2 | 5/2004 | Jackson | |
| 6,783,527 B2* | 8/2004 | Drewry et al. | 606/254 |
| 6,981,973 B2 | 1/2006 | McKinley | |
| 7,018,379 B2 | 3/2006 | Drewry et al. | |
| 7,141,051 B2 | 11/2006 | Janowski et al. | |
| 7,204,838 B2 | 4/2007 | Jackson | |
| 7,611,527 B2* | 11/2009 | Freid et al. | 606/279 |
| 7,632,293 B2* | 12/2009 | Hartmann | 606/257 |
| 7,731,749 B2* | 6/2010 | Biedermann et al. | 623/13.14 |
| 7,972,364 B2* | 7/2011 | Biedermann et al. | 606/267 |
| 8,048,124 B2* | 11/2011 | Chin et al. | 606/61 |
| 8,282,672 B2* | 10/2012 | Freudiger | 606/267 |
| 2001/0020168 A1* | 9/2001 | Hermann et al. | 606/61 |
| 2001/0025180 A1 | 9/2001 | Jackson | |
| 2003/0125741 A1* | 7/2003 | Biedermann et al. | 606/61 |
| 2003/0220642 A1* | 11/2003 | Freudiger | 606/61 |
| 2004/0167524 A1 | 8/2004 | Jackson | |
| 2004/0167525 A1 | 8/2004 | Jackson | |
| 2004/0167526 A1 | 8/2004 | Jackson | |
| 2005/0203518 A1* | 9/2005 | Biedermann et al. | 606/61 |
| 2005/0277920 A1 | 12/2005 | Slivka et al. | |
| 2006/0025771 A1 | 2/2006 | Jackson | |
| 2006/0106380 A1* | 5/2006 | Colleran et al. | 606/61 |
| 2006/0122599 A1 | 6/2006 | Drewry et al. | |
| 2006/0129147 A1* | 6/2006 | Biedermann et al. | 606/61 |
| 2006/0200136 A1 | 9/2006 | Jackson | |
| 2006/0241603 A1 | 10/2006 | Jackson | |
| 2006/0276789 A1 | 12/2006 | Jackson | |
| 2007/0055235 A1 | 3/2007 | Janowski et al. | |
| 2007/0055242 A1* | 3/2007 | Bailly | 606/61 |
| 2007/0093820 A1* | 4/2007 | Freudiger | 606/61 |
| 2007/0093821 A1* | 4/2007 | Freudiger | 606/61 |
| 2007/0161999 A1* | 7/2007 | Biedermann et al. | 606/61 |
| 2007/0208344 A1* | 9/2007 | Young | 606/61 |
| 2008/0045955 A1 | 2/2008 | Berrevoets et al. | |
| 2008/0086132 A1* | 4/2008 | Biedermann et al. | 606/61 |
| 2008/0114404 A1 | 5/2008 | Matthis et al. | |
| 2008/0125816 A1 | 5/2008 | Jackson | |
| 2008/0177321 A1 | 7/2008 | Drewry et al. | |
| 2008/0183223 A1 | 7/2008 | Jeon et al. | |
| 2008/0195159 A1 | 8/2008 | Kloss et al. | |
| 2008/0215095 A1* | 9/2008 | Biedermann et al. | 606/246 |
| 2008/0215100 A1 | 9/2008 | Matthis et al. | |
| 2010/0286731 A1* | 11/2010 | Biedermann et al. | 606/264 |
| 2013/0079824 A1* | 3/2013 | Freudiger | 606/255 |
| 2013/0079833 A1* | 3/2013 | Biedermann et al. | 606/308 |

FOREIGN PATENT DOCUMENTS

| | | |
|---|---|---|
| EP | 1 795 134 A1 | 6/2007 |
| EP | 1 900 334 A1 | 3/2008 |
| FR | 2 624 720 A1 | 6/1989 |
| WO | WO 92/03100 A1 | 3/1992 |
| WO | WO 03/041601 A1 | 5/2003 |
| WO | WO 2006/068711 A2 | 6/2006 |
| WO | WO 2006/115539 A2 | 11/2006 |

OTHER PUBLICATIONS

Claims from U.S. Appl. No. 11/854,508.
OA mailed Nov. 27, 2009 from U.S. Appl. No. 11/854,508, 13 sheets.
OA mailed May 21, 2010 from U.S. Appl. No. 11/854,508, 15 sheets.
OA mailed Dec. 7, 2010 from U.S. Appl. No. 11/854,508, 16 sheets.
OA mailed Jan. 17, 2012 from U.S. Appl. No. 11/854,508, 13 sheets.
OA mailed Jun. 1, 2012 from U.S. Appl. No. 11/854,508, 12 sheets.
Office action dated Oct. 2, 2013 for U.S. Appl. No. 13/613,739, 12 pages.

* cited by examiner

BONE ANCHORING ASSEMBLY

CROSS-REFERENCE TO RELATED APPLICATIONS

The present application claims the benefit of U.S. Provisional Patent Application Ser. No. 61/073,879, filed Jun. 19, 2008, the contents of which are hereby incorporated by reference in their entirety, and claims priority from European Patent Application EP 08 011 203.0, filed Jun. 19, 2008, the contents of which are hereby incorporated by reference in their entirety.

BACKGROUND

The application relates to a bone anchoring assembly for dynamic stabilization of bone or vertebrae.

A bone anchoring assembly with a flexible rod made of an elastomer material is known, for example, from EP 1 759 646 A1. The rod is held in the receiving part by means of a closure cap and a filling piece which presses onto the rod when the closure cap is screwed onto the receiving part. The surface of the filling piece and the bottom of the receiving part includes, for example, conical pins which press onto the rod and create an indirect form-fit connection which contributes to the frictional connection so as to hold the rod safely in place. The indirect form-fit connection is achieved by a local elastic or plastic deformation of the material of the rod. The bone anchoring element is of the type of a monoaxial screw, wherein the receiving part and the shank are not pivotably connected.

A bone anchoring assembly with a flexible rod is further known from EP 1 795 134 A1 which describes a polyaxial bone anchoring element. The receiving part and the shank are pivotably connected and a pressure element is provided to lock the angular position of the shank relative to the receiving part. The surface of the filling piece and that of the pressure element which contacts the rod has rib-like projections which press onto the flexible rod and provide a form-fit contribution to the fixation of the rod in the receiving part.

From EP 1 900 334 A1 a bone anchoring assembly of the above mentioned type is known, which includes a single part closure element instead of a closure element with a filling piece. The single part closure element is an inner screw to be screwed between the legs of the receiving part, which has an annular projection on its lower side which presses onto the flexible rod.

The bone anchoring assemblies mentioned above which use the flexible rod comprise an engagement structure to clamp the rod which has sharp edges and/or which has teeth or ribs which are arranged exactly on opposite sides of the rod in order to provide a safe locking.

With such engagement structures there is a risk of weakening the rod, if the rod diameter is small. Therefore, the known assemblies are mainly used with rods having a relatively large diameter, for example a diameter of approx. 9 mm or larger. However, there is a need for the use of bone anchoring assemblies of the type using a flexible rod which are small in size, in particular, when the implant is to be placed at a location which is exposed and not covered enough by muscles, ligaments or other soft tissue.

FR 2 624 720 discloses an osteosynthesis device including a bone anchoring element with a shank and a receiving part and a fixation rod which is not flexible but rigid, usually made of a biocompatible metal. The fixation rod is held in the receiving part by a locking cap which includes a central pin with a tip penetrating into the surface of the rigid rod. The pin with the tip serves for a provisional fixation of the rod until the locking cap is tightened.

Based on the foregoing, there is a need for a bone anchoring assembly for dynamic stabilization using a flexible rod which is smaller in size compared to the known bone anchoring assemblies while providing the same degree of safe fixation of the rod as the known bone anchoring assemblies.

SUMMARY

A bone anchoring assembly according to the disclosure includes a bone anchoring element with a shank to be anchored in a bone or a vertebra and a receiving part for receiving a rod and a rod which is at least party flexible, the flexible section being made of a polymer material. The rod connects at least two bone anchoring elements. The bone anchoring element includes a two-piece locking device for allowing a clamping of the rod in two steps by means of pins with a rounded tip.

The bone anchoring assembly can be used, for example, with flexible elastomer rods, which have diameters below 9 mm. When using a small diameter rod, also the bone anchoring element, in particular the receiving part, can be downsized. Therefore, a low profile implant is provided which causes the irritation of surrounding body material to be small.

The pins which contribute to clamp the rod have a rounded tip of the uppermost portion. Hence, the integrity of the surface of the rod is not violated, since the pins do not scratch the structure. The two-step clamping of the rod is safe and effective.

Mechanical stops are provided for preventing a penetration of the clamping pins into the surface of the rod due to limitation of the pressure force.

Further features and advantages will become apparent from the description of embodiments by means of the accompanying drawings.

DETAILED DESCRIPTION OF THE INVENTION

Figures 1, 2:
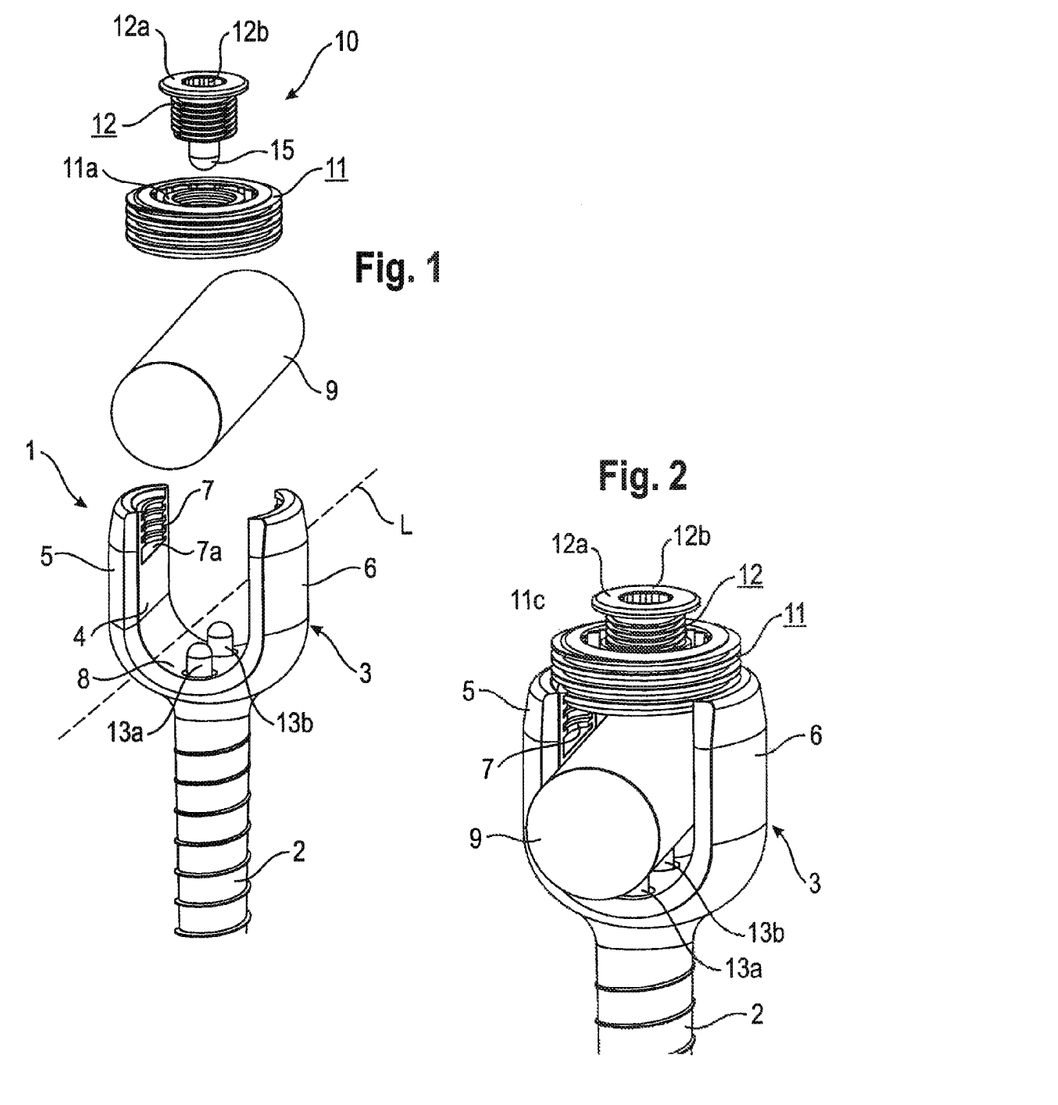
FIG. 1 shows a perspective exploded view of the bone anchoring assembly according to a first embodiment.
FIG. 2 shows a perspective view of the bone anchoring assembly according to FIG. 1 in an assembled state before final clamping of the rod.

As shown in FIGS. 1 and 2 the bone anchoring assembly according to a first embodiment includes a bone anchoring element 1 in the form of a monoaxial bone screw having a shank 2 with a bone thread and a tip at one end and a receiving part 3 at the opposite end. The receiving part 3 is substantially cylindrically-shaped and includes a substantially U-shaped recess 4 forming two free legs 5, 6 defining a channel for the insertion of the rod. An internal thread 7 is provided on the legs. The bottom of the U-shaped recess forms a seat 8 for receiving a rod 9. The rod 9 is used to connect several bone anchoring elements. To secure the rod 9 in the recess 4, a two piece locking device 10 is provided which includes an outer locking screw 11 and an inner locking screw 12. The locking device can be screwed between the legs 5, 6. At the lower end of the internal thread 7 the receiving part 3 includes a shoulder 7a for forming a stop for the screwing-in for the outer locking element 11.

On the surface of the seat 8, more precisely on the bottom of the U-shaped recess 4, two pins 13a, 13b are provided which are located preferably at both ends of the channel. The uppermost parts of the pins are located on a line which is parallel to the longitudinal axis L of the channel. The pins 13a, 13b are substantially cylindrical and their free end is rounded, preferably semi-spherical. More specifically, the pins are longitudinal rod-shaped pins with a rounded free end.

Figure 11:
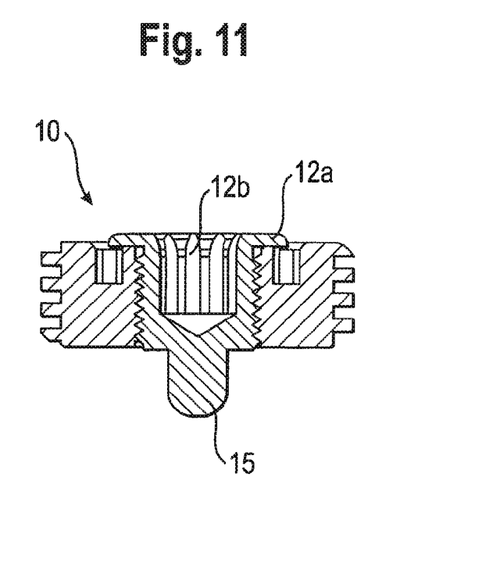
FIG. 11 shows a sectional view of the locking device with the inner locking screw tightened.
Figure 12:
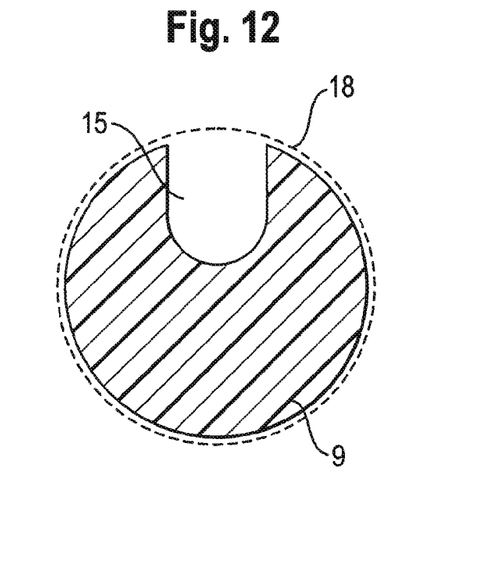
FIG. 12 shows a sectional view of the rod according to the first embodiment, the section being taken perpendicular to the rod axis, showing schematically the engagement of the pin of the inner locking screw.

The outer locking screw 11 of the locking device 10 includes a threaded coaxial bore 11a into which the inner locking screw 12 can be screwed. As best seen in FIGS. 11 and 12 the outer locking screw 11 has an external thread 11b, which is preferably in the form of a flat thread cooperating with a flat thread 7 at the inner side of the legs 5, 6 of the receiving part to prevent splaying of the legs when the outer locking screw 11 is screwed-in. The outer locking screw 11 further includes an annular coaxial recess 11c with an engagement structure for engagement with a screwing-in tool (not shown). The inner locking screw 12 includes at one end an annular projection 12a, the diameter of which is slightly larger than the inner diameter of the coaxial recess 11c. As shown in FIG. 11, when the inner locking screw 12 is screwed-in, the annular projection 12a abuts against the inner edge of the coaxial recess 11c preventing further advancement of the inner screw. Hence, a stop is provided for the introduction of the inner locking screw 12 into the outer locking screw 11. Of course, the stop for the screwing-in of the inner locking screw can be realized otherwise. The length of the threaded portion of the inner locking screw corresponds to the length of the threaded bore of the outer locking screw 11. The inner locking screw further has a coaxial circular recess 12b with an engagement structure for screwing-in the inner locking screw 12. On its side opposite to the annular projection 12a the inner locking screw 12 includes a coaxial pin 15 for pressing onto the rod 9. As shown in FIG. 11, when the inner locking screw is screwed-in to the outer locking screw, the coaxial pin 15 projects from the substantially flush lower side of the locking device. The pin 15 is preferably cylindrical with a semi-spherical free end, more specifically, the pin 15 is a longitudinal rod-shaped pin with a rounded free end and corresponds in its dimension substantially to the dimensions of the pins 13a and 13b of the receiving part. The pin-shaped projections 13a, 13b in the channel are arranged axially offset to the cylinder axis of the pin-shaped projection 15 on the second locking screw.

The bone anchoring element 1 and the locking device 10 are made of a biocompatible material, such as, for example, titanium or stainless steel or another biocompatible material, for example PEEK.

The rod 9 is made at least in part of a flexible biocompatible material, preferably of a plastic material and in particular of an elastomer material. Such a material can be based on, for example, polycarbonate-polyurethane or polycarbonate-urethane (PCU). However, other materials are also applicable, for example styrene-block-isobutylene-block-styrene (SIBS) and other elastomers. The rod does not need to be made totally of one single material but can comprise several materials and inner structures and/or sections with different flexibility/rigidity. The flexible section is the section which is to be clamped in the receiving part. The diameter of the rod 9 can be any of the usual diameters of rods for stabilisation of the spine, in particular diameters from 4.5 mm-9 mm.

Figure 3:
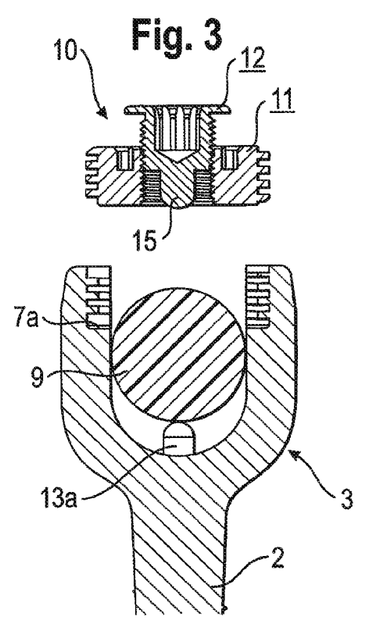
FIG. 3 shows a sectional view of the bone anchoring assembly according to the first embodiment, the section being taken perpendicular to the rod axis, wherein the locking device is not yet inserted.
Figure 4:
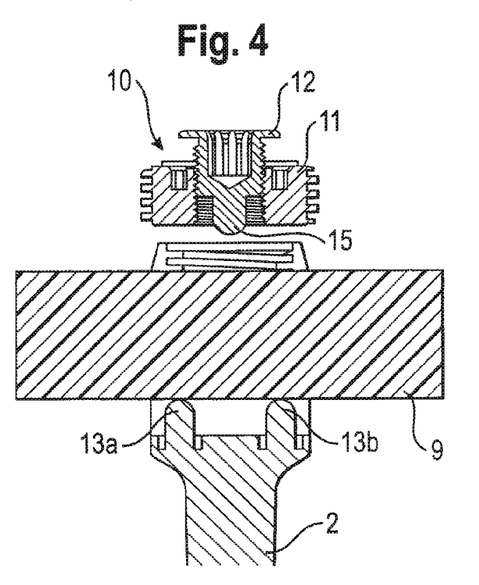
FIG. 4 shows a sectional view of the bone anchoring assembly according to FIG. 3, the section being taken in a plane containing the rod axis.

In use, first at least two bone anchoring elements 1 are screwed into adjacent vertebrae, for example into the pedicles. At least one of the bone anchoring elements is formed according to the first embodiment. Thereafter, the rod 9 is inserted into the receiving part 3 and fixed. The procedure of fixation is now explained with reference to FIGS. 3 to 9. As shown in FIGS. 3 and 4 the inner locking screw 12 is screwed into the outer locking screw only to an extent such that only a small part of the pin 15 projects from the lower side of the outer locking screw 11. The rod 9 is inserted into the channel until it rests onto the pins 13a, 13b projecting from the seat 8.

Figure 5:
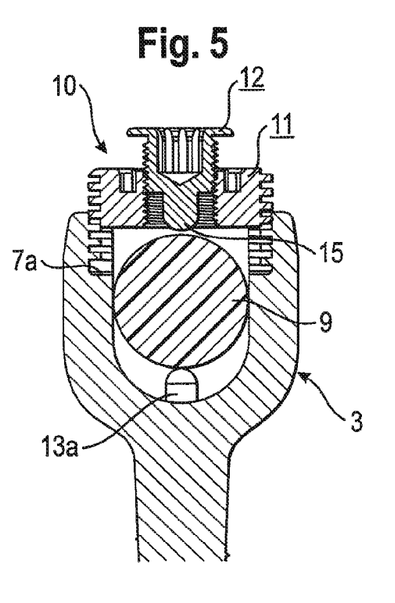
FIG. 5 shows a sectional view of the bone anchoring assembly according to FIG. 3, where the locking device is inserted but not yet tightened.

Then, as shown in FIG. 5 the locking device 10 is inserted between the legs in such a way that the pin 15 is directed against the rod 9.

Figure 6:
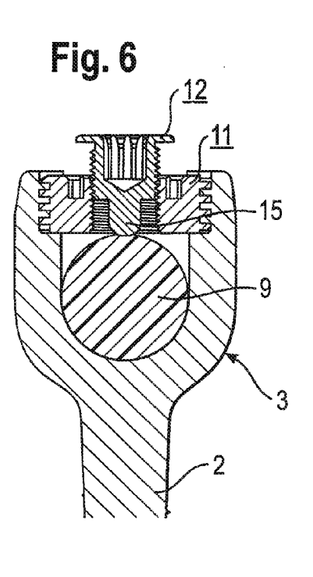
FIG. 6 shows a sectional view of the anchoring device of FIG. 3, the section being taken perpendicular to the rod axis, wherein the outer locking screw of the locking device is tightened and the inner locking screw of the locking device is not yet tightened.
Figure 7:
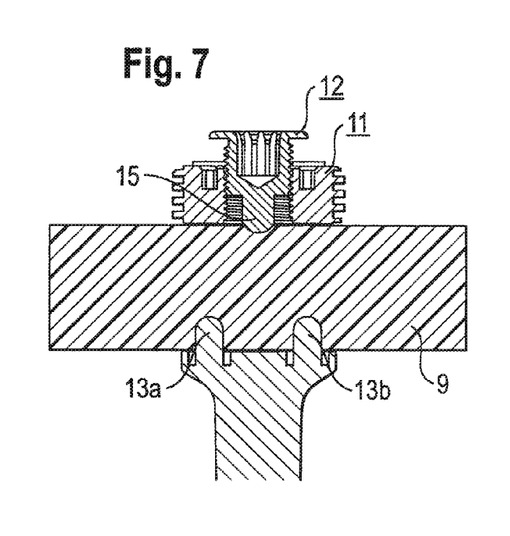
FIG. 7 shows a sectional view of the bone anchoring assembly shown in FIG. 6.

As shown in FIGS. 6 and 7, when the outer locking screw 11 is screwed-in completely between the legs 5, 6 until it rests on the shoulder 7a of the receiving part, the pins 13a, 13b are pressing into the surface of the rod until they are fully immersed in the surface of the rod due to the local flow of the material of the rod which leads to a local elastic and/or plastic deformation of the rod.

Figure 8:
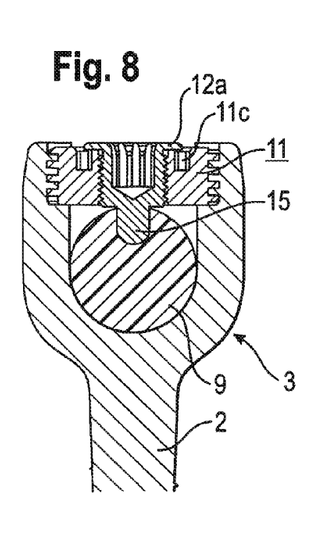
FIG. 8 shows a sectional view, the section being taken perpendicular to the rod axis of the bone anchoring assembly in a fully tightened state of the locking device.
Figure 9:
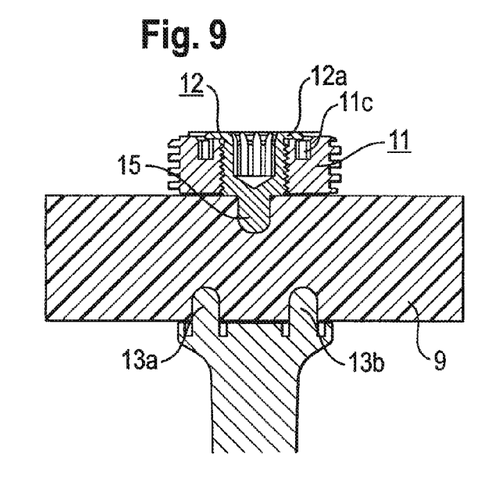
FIG. 9 shows a sectional view of the bone anchoring assembly of FIG. 8, the section being taken in a plane containing the rod axis.
Figure 10:
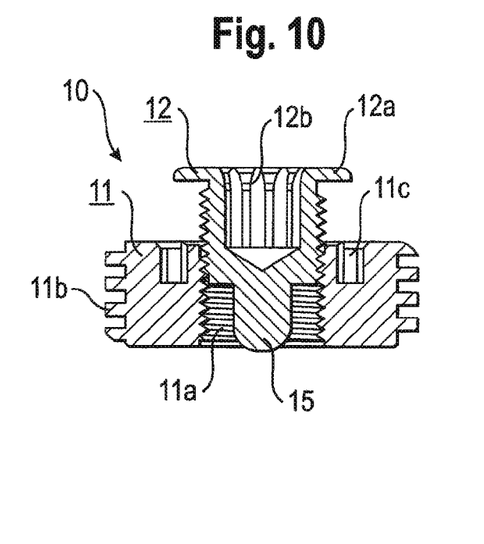
FIG. 10 shows an enlarged sectional view of the locking device with the inner locking screw not yet tightened.

Then, as shown in FIGS. 8 and 9, the inner locking screw 12 is tightened. During tightening of the inner locking screw 12 until the projection 12a abuts against the outer locking screw 11, the pin 15 presses onto the opposite side of the surface of the rod and is immersed into the surface of the rod. Due to the mechanical stops in form of the shoulder 7a in the receiving part and in form of the cooperation of the annular projection 12a of the inner locking screw with the edge of the coaxial recess 11c of the outer locking screw, the pressure force exerted by the pins 13a, 13b, 15 onto the surface of the rod is well-defined and cannot be exceeded. The dimension of the pins, in particular their height, their diameter and the radius of the free end portion is designed such that under a given pressure force which is limited by the stops, the pins do not violate the integral structure of the rod.

As can be seen in particular in FIG. 9, the arrangement of the pin fixation seen in a direction perpendicular to the longitudinal axis of the rod is a three-point fixation which is particularly safe. Accordingly, there is no clamping on locations which are exactly on opposite sides of the rod which may cause the danger of violating the integral structure of the rod at the clamping site.

As shown in FIGS. 6 to 9 the fixation of the rod takes place in two steps. In the first step, the rod is fixed from below by means of the pins 13a, 13b. In the second step, the rod is fixed from above by the means of the pin 15. This results in a safe and effective fixation.

Figure 13:
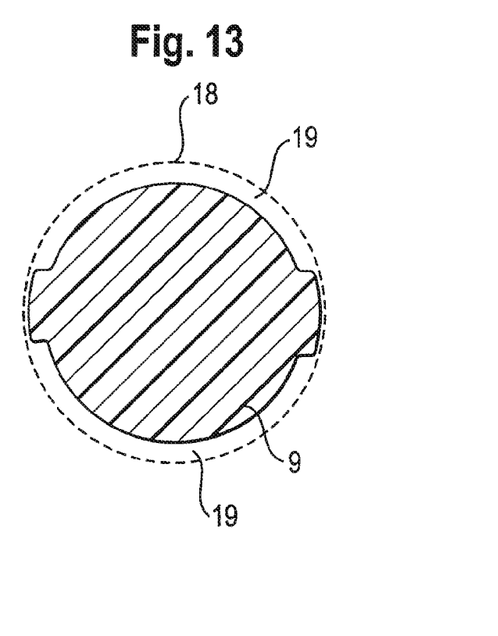
FIG. 13 shows a sectional view of the rod, the section being taken perpendicular to the rod axis in a case where two rib-like teeth engage the rod at opposite sides.

As shown schematically in FIG. 12 the surface area of the rod in an unclamped condition and in a section perpendicular to the rod axis (dashed line 18) is nearly unchanged when the pin 15 and the pins 13a, 13b are immersed into the rod. Compared thereto, as shown in FIG. 13, a clamping of the rod from opposite sides by ribs 19 would lead to a considerable reduction of the surface area within the receiving part (reduction from dashed line to full line). With the clamping according to the disclosure, as shown in FIG. 12, the reduction of the surface area is significantly less than with ribs. Since the pins 13a, 13b in the channel are axially offset to the pin 15 on the second locking element, the cross section of the rod at the clamping site can be maximized.

A second embodiment of the bone anchoring assembly will now be described with reference to FIGS. 14 to 19. Parts which are identical to the previously described embodiment are indicated with the same reference numerals and the description thereof will not be repeated.

Figures 14, 15:
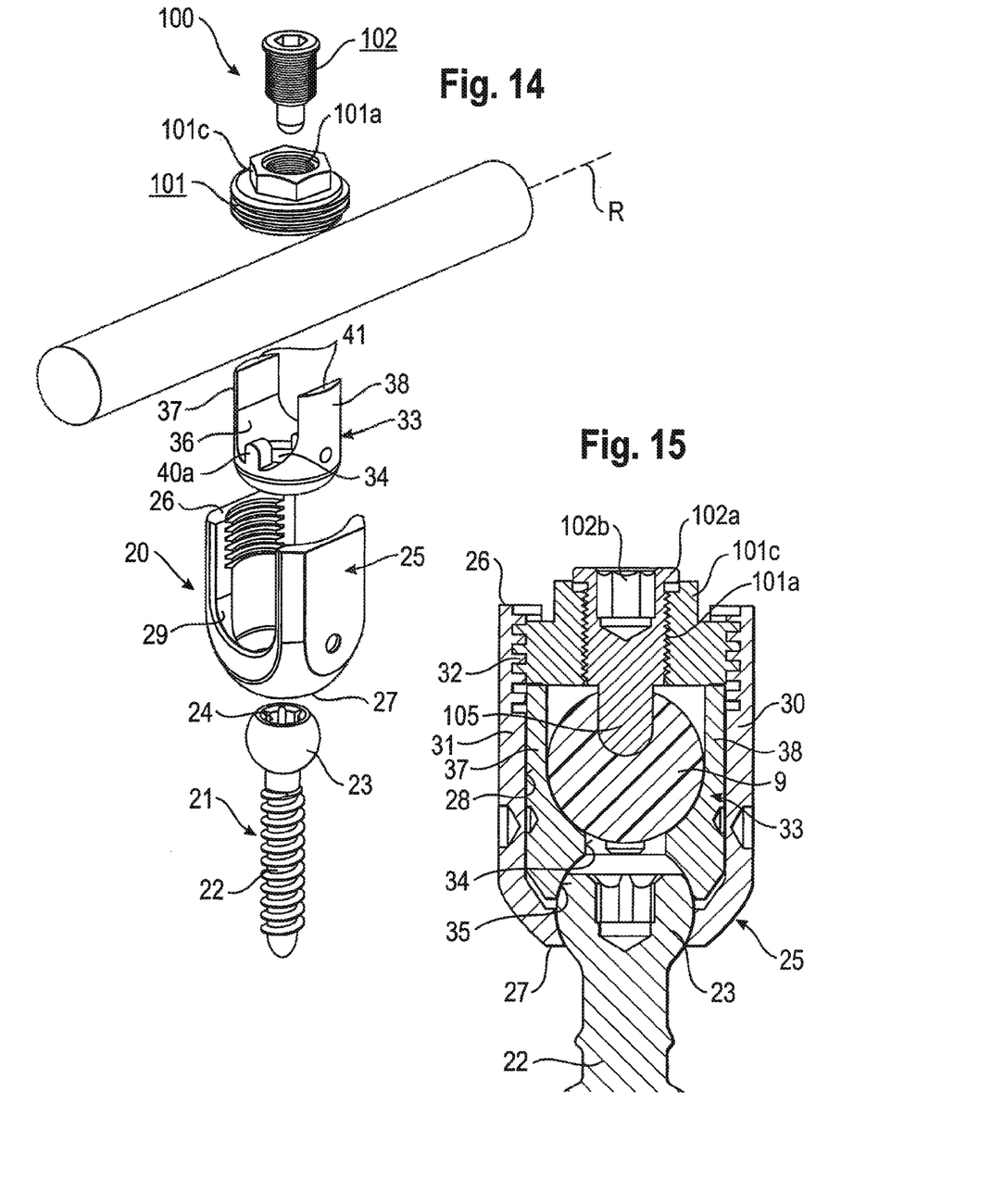
FIG. 14 shows a second embodiment of the bone anchoring assembly in a perspective exploded view.
FIG. 15 shows a sectional view of the bone anchoring assembly according to the second embodiment, the section being taken perpendicular to the rod axis.
Figure 16:
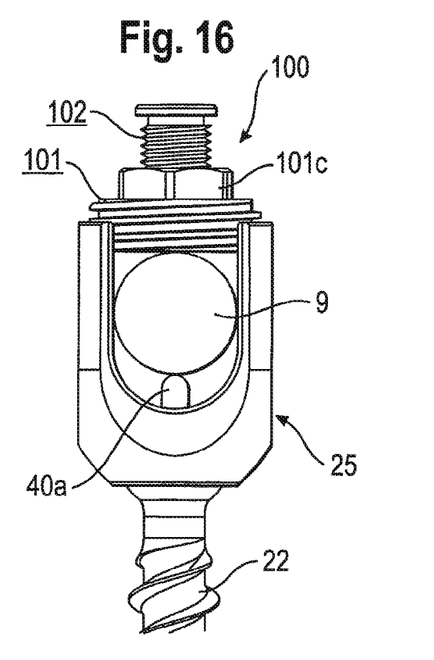
FIGS. 16 and 17 show a side view seen along the rod axis and a sectional view along the rod axis of the bone anchoring assembly according to the second embodiment before tightening the inner locking device.
Figure 17:
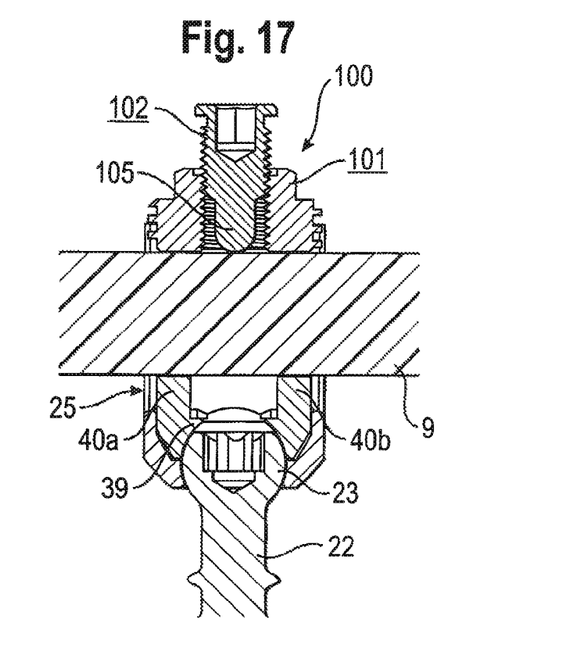

The bone anchoring assembly includes a bone anchoring element 20, the rod 9 which is identical to the previously described rod and a locking device 100. The bone anchoring element includes a bone anchor 21 having a shank 22 to be anchored in the bone and a spherically-shaped head 23 with a recess 24 at the free end for screwing-in the anchor into the bone. The receiving part 25 is substantially cylindrical and includes a first end 26 and a second end 27 and a coaxial bore 28 extending from the first end 26 to the second end 27 and tapering in an area near the second end such that, as shown in FIG. 15 the head 23 of the anchor is pivotably held in the receiving part at the second end 27. Furthermore, the receiving part 25 includes a U-shaped recess 29 extending from the first end 26 in the direction of the second end 27. With the U-shaped recess 29 two free legs 30, 31 are formed which include an internal thread 32.

A pressure element 33 is provided which is substantially cylindrical and dimensioned such that it can be moved within the bore 28 of the receiving part 25. The pressure element 33 has a coaxial bore 34 extending through the pressure element and allowing to guide a screwing-in tool therethrough for screwing-in the anchor 21. It further includes a spherical recess 35 which is adapted to receive the spherical head 23 of the anchor 21. Further, the pressure element 33 includes a substantially U-shaped recess 36 extending from its free end in the direction of the spherical recess 35. By means of the U-shaped recess 36 two free legs 37, 38 are formed which form the lateral walls of a channel for receiving the rod. On the bottom 39 of the channel two pins 40a, 40b are provided which are arranged in a similar way as the pins 13a, 13b of the first embodiment and which are located in this embodiment at both sides of the bore 34. In the embodiment shown, the pins have a substantially quadrangular shape and their uppermost portions are semi-cylindrical. However, they can have any shape as long as the uppermost portion is rounded as described in the first embodiment. The uppermost portions of the pins 40a, 40b are located on a line which is parallel to the longitudinal axis R of the rod.

As shown in particular in FIG. 15 the pressure element 33 is sized in such a way that the legs 37, 38 extend slightly above the surface of the rod when the rod is inserted into the channel and the pins 40a, 40b are immersed into the surface of the rod 9.

In contrast to the first embodiment the internal thread 32 of the receiving part does not have a shoulder on its end but the stop for the locking device is provided by the upper edge 41 of the legs 37, 38 of the pressure element 33.

The locking device 100 includes as in the first embodiment an outer locking screw 101 and an inner locking screw 102. The outer locking screw 101 differs from the outer locking screw 11 of the first embodiment only in that it includes instead of the recess 11c for screwing-in a projecting engagement structure 101c for engagement with a screwing-in tool. However, outer locking screw 101 can also be formed identical to the outer locking screw 11 of the first embodiment. The outer locking screw 101 also includes a coaxial threaded bore 101a into which the inner locking screw 102 can be screwed. The inner locking screw 102 is similar to the inner locking screw 12 of the first embodiment. It includes an annular projection 102a at its one end and a recess 102b for screwing-in.

The inner locking screw 102 includes at its other end a pin 105 which is shaped like the pin 15 according to the first embodiment. When the inner locking screw 102 is screwed-in into the outer locking screw 101, the annular projection 102a abuts against a part of the engagement structure 101c whereby a stop is formed preventing further screwing-in of the inner locking screw 102. In this state only the pin 105 projects from the lower side of the locking device.

Figure 18:
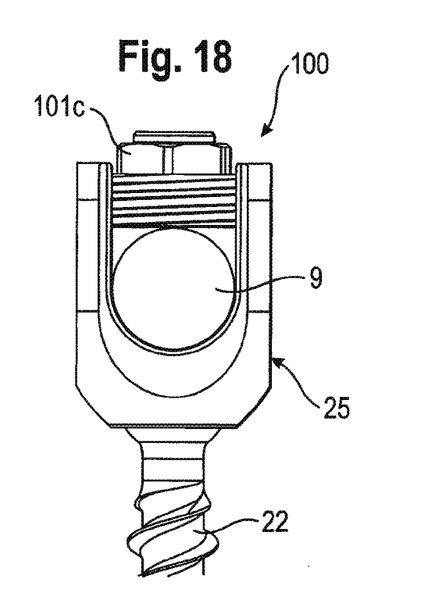
FIGS. 18 and 19 show the bone anchoring assembly according to FIGS. 16 and 17, respectively, when the inner locking device is tightened.
Figure 19:
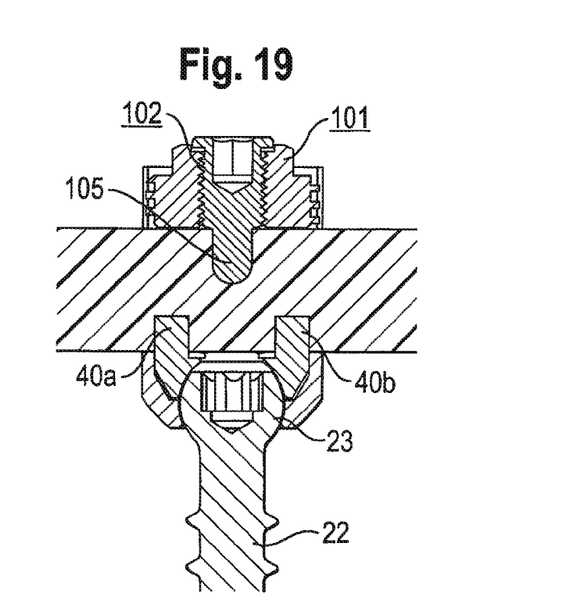

In use, at first, at least two bone anchoring elements are screwed into adjacent bone parts or vertebrae. In this condition the pressure element 33 does not fix the angular position of the anchor with respect to the receiving part and the receiving part can be aligned to receive the rod 9. Then, the fixation is described with respect to FIGS. 16 to 19. As in the first embodiment the locking device 100 is assembled in such a way that the inner locking screw 102 is not fully screwed into the outer locking screw 101. The rod is inserted into the channel of the pressure element such that it rests onto the pins 40a, 40b. Then, the locking device 100 is tightened by means of screwing-in the first locking screw 101 until it presses onto the upper edge 41 of the pressure element. Since the legs 37, 38 slightly project above the surface of the rod, the whole pressure element with the rod is pressed downward to fix the head 23 in the receiving part 25 so that it can no longer pivot. During this process, when the rod is pressed into the pressure member, the pins 40a, 40b press onto the lower surface of the rod thereby immersing into the lower surface and fixing the rod in the U-shaped channel of the pressure element. Thereafter, as shown in FIGS. 18 and 19, the inner locking screw 102 is tightened until the annular projection 102 abuts against the engagement structure 101c. As in the first embodiment the dimension is such that in this condition the pin 105 is pressed onto and immersed in the surface of the rod without any excess force. Hence, the fixation is as in the first embodiment a two-step fixation which is safe and effective. In the first step also the head 23 is locked within the receiving part.

Several modifications are conceivable. For example, the number of pins in the bottom of the channel of either the receiving part or the pressure element may vary. In some cases more than two pins might be of advantage. The shape of the pins can also vary. However, the height of the pin and the radius of the uppermost rounded portion must be designed such that there is no violation of the integral structure of the rod, while simultaneously providing safe fixation.

Modifications of the locking device are also conceivable. For example, the two-part locking device may consist of an outer nut and an inner screw with the inner screw having the pin. The engagement between the receiving part and the locking device must not be a threaded engagement, other forms of engagement such as a bayonet coupling are conceivable.

All other kinds of polyaxial bone anchoring devices known may be conceivable which can be modified so as to have the pins described above. For example, a polyaxial screw, where the bone anchor 21 is inserted from below, a so-called bottom-loader, may be also used.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring assembly comprising:
    a bone anchoring element having a shank to be anchored to a bone or a vertebra, and a receiving part for receiving a rod, the receiving part having a channel with an approximately U-shaped cross-section with two free legs, wherein the shank and the receiving part are configured to be pivotably connected together;
    a rod having a flexible section made at least partly of a polymer material and configured to be received in the channel;
    a pressure element configured to exert pressure onto an end portion of the shank to lock the angular position of the shank relative to the receiving part, wherein the pressure element comprises a channel to receive the rod and wherein the channel of the pressure element is configured to be aligned with the channel of the receiving part;
    at least one pin-shaped projection in the channel of the pressure element;
    a first locking element configured to be located between and engage the legs and to engage the rod when the rod is in the channel;
    wherein the at least one pin-shaped projection in the channel of the pressure element is immersed in a bottom portion of the flexible section of the rod, without violating the integrity of a surface of the flexible section of the rod where the at least one pin-shaped projection of the pressure element is immersed, when tightening the first locking element; and
    a second locking element configured to be located inside and engage the first locking element and to act independently from the first locking element, the second locking element comprising a pin-shaped projection configured to be immersed in a top portion of the flexible section of the rod;
    wherein when the second locking element is tightened to further secure the rod in the channel of the pressure element, the projection of the second locking element is immersed in the top portion of the flexible section of the rod without violating the integrity of a surface of the flexible section of the rod where the projection is immersed.

2. The bone anchoring device of claim 1, wherein a plurality of pin-shaped projections are arranged on a bottom of the channel of the pressure element.

3. The bone anchoring device of claim 2, wherein the pin-shaped projections are arranged along a longitudinal axis of the rod when the rod is in the channel of the pressure element.

4. The bone anchoring assembly of claim 1, wherein the first locking element is an outer locking screw configured to be threaded to an internal thread provided on the legs of the receiving part.

5. The bone anchoring assembly of claim 4, wherein the first locking element comprises a coaxial threaded bore and the second locking element is an inner screw configured to be screwed into said bore.

6. The bone anchoring assembly of claim 1, wherein each of the pin-shaped projection of the second locking element and the at least one pin-shaped projection of the pressure element is a longitudinal rod-shaped pin and the surface of the pin which first contacts the rod, is rounded.

7. The bone anchoring assembly of claim 1, wherein a plurality of pin-shaped projections are arranged on a bottom of the channel of the pressure element, and wherein the pin-shaped projections are provided at both outer ends of the channel of the pressure element.

8. The bone anchoring assembly of claim 1, wherein a stop is provided on the first locking element which limits the insertion of the second locking element into the first locking element.

9. The bone anchoring assembly of claims 1, wherein a stop is provided other than the rod which limits the insertion of the first locking element into the receiving part.

10. The bone anchoring assembly of claim 1, wherein the polymer material of the rod is an elastomer material.

11. The bone anchoring assembly of claim 1, wherein the at least one pin-shaped projection provided in the channel of the pressure element is axially offset from the pin-shaped projection provided at the second locking element along a longitudinal axis of the rod when the rod is in the channel of the pressure element.

12. The bone anchoring assembly of claim 1, wherein the second locking element comprises only one pin-shaped projection configured to be immersed in the flexible section of the rod.

13. The bone anchoring assembly of claim 1, wherein the receiving part has a central axis, and wherein the pin-shaped projection of the second locking element is configured to be immersed in the flexible section of the rod along the central axis.

14. A bone anchoring assembly comprising:
    a bone anchoring element having a shank to be anchored to a bone or a vertebra;
    a receiving part for receiving a rod, the receiving part comprising a first end, a second end, and a channel with an approximately U-shaped cross-section with two free legs extending from the second end to the first end;
    a rod having a flexible section made at least partly of a polymer material and configured to be received in the receiving part, the rod defining a longitudinal axis;
    a first locking element configured to be located between and engage the legs and to engage the rod when the rod is in the channel;
    a second locking element configured to be located inside and engage the first locking element and to act independently from the first locking element, the second locking element comprising a pin-shaped projection configured to be immersed in a top portion of the flexible section of the rod without violating the integrity of a surface of the flexible section of the rod when the second locking element is tightened;

at least two pin-shaped projections provided in the channel, such that when the rod is in the channel and the first locking element is tightened, the two pin-shaped projections are immersed in a bottom portion of the flexible section of the rod without violating the integrity of the surface of the flexible section of the rod;

wherein the pin-shaped projection of the second locking element and the at least two pin-shaped projections are spaced apart in a direction of the longitudinal axis of the rod when the rod is in the channel.

15. The bone anchoring assembly of claim 14, wherein the shank and the receiving part are pivotably connected and wherein a pressure element is provided which exerts pressure onto the end portion of the shank to lock the angular position of the shank relative to the receiving part.

16. The bone anchoring assembly of claim 15, wherein the pressure element comprises a channel to receive the rod and wherein the channel of the pressure element is aligned with the channel of the receiving part.

17. The bone anchoring assembly of claim 16, wherein the at least two pin-shaped projections are provided in the channel of the pressure element.

18. A method of attaching a bone anchoring assembly to a bone or a vertebra, the bone anchoring assembly comprising a bone anchoring element having a shank to be anchored to a bone or a vertebra, a receiving part for receiving a rod, the receiving part having a channel with an approximately U-shaped cross-section with two free legs, wherein the shank and the receiving part are configured to be pivotably connected together, a rod having a flexible section made at least partly of a polymer material and configured to be received in the channel, a pressure element configured to exert pressure onto an end portion of the shank to lock the angular position of the shank relative to the receiving part, wherein the pressure element comprises a channel to receive the rod and wherein the channel of the pressure element is configured to be aligned with the channel of the receiving part, at least one pin-shaped projected in the channel of the pressure element, a first locking element configured to be located between and engage the legs and to engage the rod when the rod is in the channel, wherein the at least one pin-shaped projection in the channel of the pressure element is immersed in a bottom portion of the flexible section of the rod, without violating the integrity of a surface of the flexible section of the rod where the at least one pin-shaped projection of the pressure element is immersed, when tightening the first locking element, and a second locking element configured to be located inside and engage the first locking element and to act independently from the first locking element, the second locking element comprising a pin-shaped projection configured to be immersed in a top portion of the flexible section of the rod, wherein when the second locking element is tightened to further secure the rod in the channel of the pressure element, the projection of the second locking element is immersed in the top portion of the flexible section of the rod without violating the integrity of a surface of the flexible section of the rod where the projection is immersed, the method comprising:

attaching the bone anchoring element to a bone or vertebra;
inserting the pressure element into the receiving part;
inserting the rod in the channel of the pressure element;
tightening the first locking element to cause the at least one pin-shaped projection in the channel of the pressure element to immerse in the bottom portion of the flexible section of the rod without violating the integrity of the surface of the flexible section of the rod where the projection is immersed to secure the rod in the channel; and
tightening the second locking element to cause the pin-shaped projection of the second locking element to immerse in the top portion of the flexible section of the rod without violating the integrity of the surface of the flexible section of the rod where the projection is immersed to further secure the rod in the channel.

* * * * *